(12) United States Patent
Gabriel et al.

(10) Patent No.: US 6,462,221 B1
(45) Date of Patent: Oct. 8, 2002

(54) SYNTHESIS OF NITROALCOHOL DIASTEREOMERS

(75) Inventors: Richard L. Gabriel, Swampscott; Adel M. Moussa, Burlington; Sharon Fitzhenry, Marblehead; Changhua Liu, Carlisle; David A. Swanson, Lexington; Brittany La, Lawrence; Salah Zahr, Acton; Yesh P. Sachdeva, Concord; Jurjus Jurayj, Acton, all of MA (US)

(73) Assignee: Pharm-Eco Laboratories, Inc., Devens, MA (US)

( * ) Notice: Subject to any disclaimer, the term of this patent is extended or adjusted under 35 U.S.C. 154(b) by 0 days.

(21) Appl. No.: 09/574,620

(22) Filed: May 19, 2000

Related U.S. Application Data

(63) Continuation-in-part of application No. 09/510,805, filed on Feb. 23, 2000, now abandoned.
(60) Provisional application No. 60/121,312, filed on Feb. 23, 1999, and provisional application No. 60/135,344, filed on May 21, 1999.

(51) Int. Cl.[7] ...................... C07C 205/02; C07C 215/08; C07B 57/00
(52) U.S. Cl. .................. 560/22; 564/355; 562/402; 562/437
(58) Field of Search ............... 560/22; 564/355; 562/402, 437

(56) References Cited

U.S. PATENT DOCUMENTS

| | | | |
|---|---|---|---|
| 5,000,794 A | 3/1991 | Kulprathipanja | 127/55 |
| 5,475,138 A | * 12/1995 | Pal et al. | 564/342 |
| 5,889,186 A | 3/1999 | Gattuso | 564/304 |

FOREIGN PATENT DOCUMENTS

| | | |
|---|---|---|
| WO | WO 96/01788 | 1/1996 |
| WO | WO 97/45185 | 12/1997 |

OTHER PUBLICATIONS

Database CAPLUS on STN, Acc. No. 1997:259211, Francotte et al., 'Applications of simulated moving bed chromatography to the separation of the enantiomers of chiral drugs.' J. Chromatotgr., A, (1997), 769(1), pp. 101–107 (abstract).*

Database CAPLUS on STN, Acc. No. 1999:164888, Mazzotti et al., 'Separation of fine chemicals by continuous SMB chromatography.' Funda. Adsorpt., [conf.], 6th (1998), pp. 377–382 (abstract).*

Adachi, S., "Simulated moving–bed chromatography for continuous separation of two components ants application to bioreactors," *Jour. of Chromatography A* 658:271–282 (1994).

Pais, L.S. et al., "Separation of 1,1'–bi–2–naphthol enantiomers by continuous chromatography in simulated moving bed," *Chemical Engineering Science*, 52(2) :245–257 (1997).

Nagamatsu, Shinji et al., "Optical resolution of a pharmaceutical intermediate by Simulated Moving Bed," *Chiral Europa* (1996).

Gattuso, M.J. et al., "Simulated Moving Bed Technology—The Preparation of Single Enantiomer Drugs," *Chemistry Today*, (1996, Nov./Dec.).

Strube, J. et al, "Comparison of Batch Elution and Continuous Simulated Moving Bed Chromatography," *Organic Process Research and Development* 2:305–319 (1998).

Hiroshi, Harada, "3–Amino–2–Hdyroxy–1–Nitrobutane Derivative and Production of Alpha–Hdyroxy–Beta–Amino Acid," *Patent Abstracts of Japan*, vol. 014, No. 236 (c–0720) (1990).

* cited by examiner

Primary Examiner—Brian J. Davis
(74) Attorney, Agent, or Firm—Hamilton, Brook, Smith & Reynolds, P.C.

(57) ABSTRACT

The present invention relates to a method of preparing a 1-nitro-3-substituted-3-amino-2-propanol diastereomer represented by Structural Formula I:

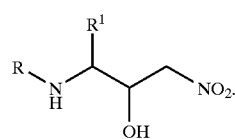

In Structural Formula I, R is an amine protecting group, and $R^1$ is an amino acid side-chain, a protected amino acid side-chain, a substituted or unsubstituted aliphatic group, a substituted or unsubstituted aromatic group, a substituted or unsubstituted heteroaromatic group, a substituted or unsubstituted aralkyl or a substituted or unsubstituted heteroaralkyl group. The method involves contacting a 1-nitro-3-substituted-3-amino-2-propanone with a reducing agent to form a mixture of 1-nitro-3-substituted-3-amino-2-propanol diastereomers. The 1-nitro-3-substituted-3-amino-2-propanol diastereomers are then separated by simulated moving bed chromatography to obtain one or more 1-nitro-3-substituted-3-amino-2-propanol diastereomer.

12 Claims, 10 Drawing Sheets

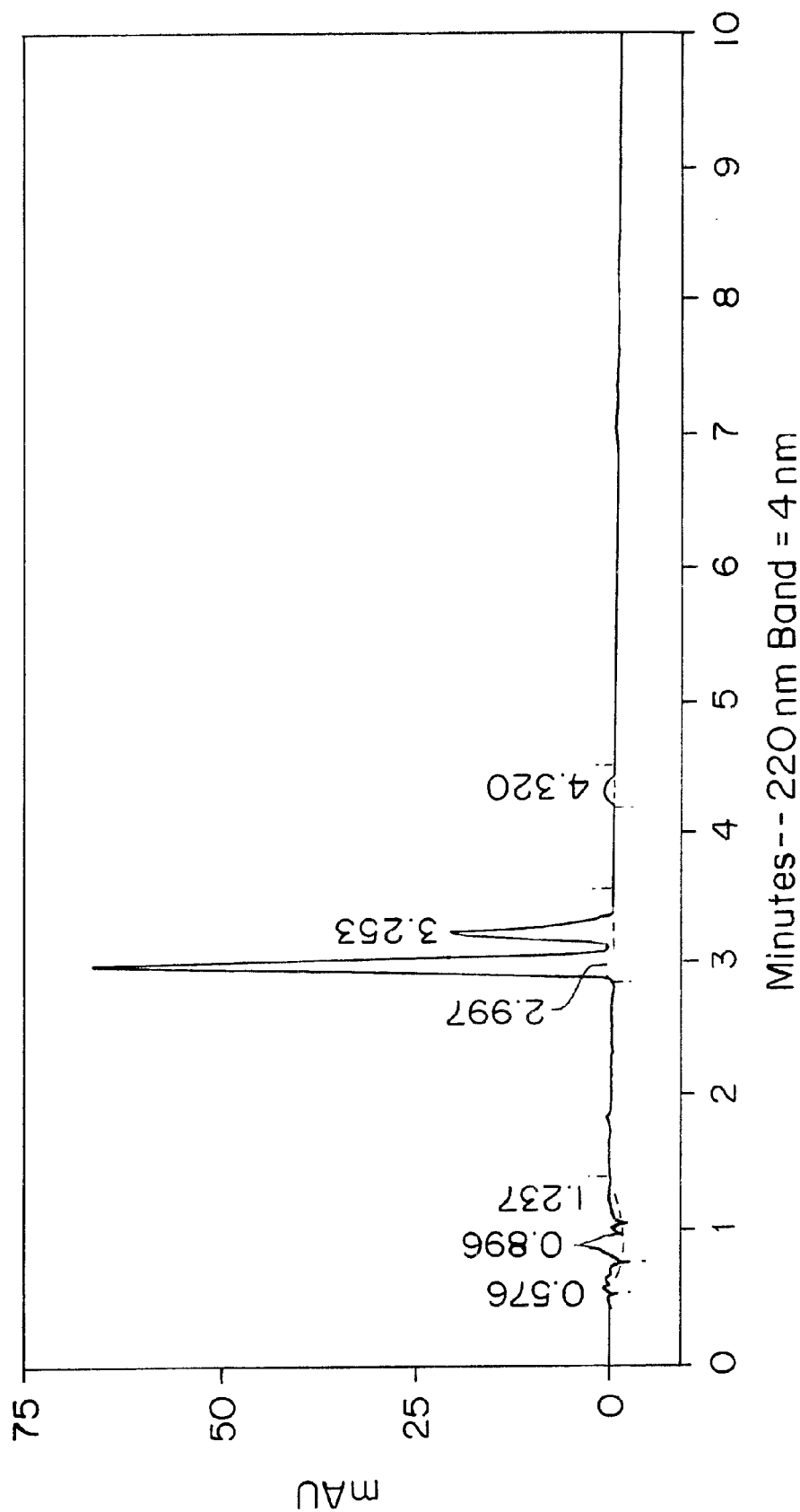

SYNTHESIS OF NITROALCOHOL DIASTEREOMERS

RELATED APPLICATION

This application is a continuation-in-part of U.S. application Ser. No. 09/510,805, filed on Feb. 23, 2000 now abandoned which claims the benefit of U.S. Provisional Application No. 60/121,312, filed Feb. 23, 1999 and U.S. Provisional Application No. 60/135,344, filed on May 21, 1999, the entire teachings of which are incorporated herein by reference.

BACKGROUND OF THE INVENTION

It is often desirable to obtain a stereochemically pure form of a molecule. For example, pharmaceuticals, which interact with a specific target, are often more potent and/or have less deleterious side effects when they are administered in their stereochemically pure form.

Diastereomers can be synthesized using asymmetric synthetic techniques. However, asymmetric synthesis can require expensive reagents or have other limitation based on the specific molecules (e.g., difficulty in recrystallizing the product).

Another method of obtaining a diastereomerically pure compound is to selectively recrystallize the desired diastereomer or a synthetic precursor, thereof. However, diastereomers, such as 1-nitro-3-substituted-3-amino-2-propanol diastereomer, are difficult, if not impossible, to separate by crystallization. Even where crystallization is possible, it only allows for recovery of one diastereomer without additional processing steps, and recovery of the desired diastereomer is often low and purity is difficult to control.

Diastereomers can be resolved chromatographically. Unfortunately, conventional preparative chromatography requires a large amount of solvent, and can be an impractical way to produce clinical trial quantities of product. In addition, simulated moving bed separations have higher throughput and are more cost efficient than conventional preparative chromatography.

Simulating moving bed chromatography has been applied to the separation of C8 hydrocarbons (see Broughton, *Chem. Eng. Prog.* (1968), 64:60).; the separation of fructose and glucose by adsorption on a zeolite solid phase (see Kieprathipanja, U.S. Pat. No. 5,000,794); and the separation of enantiomers using a chiral solid support (see Gattuso, et al., *Chemistry Today* (1996), p. 17 and Gattuso, U.S. Pat. No. 5,889,186). However, application of simulated moving bed technology to any specific group of chemical compounds often is unpredictable.

An improved method of making useful diastereomerically pure synthetic intermediates would help meet the demand for stereochemically pure compounds in the pharmaceutical and other industries.

SUMMARY OF THE INVENTION

The present invention relates to a method of preparing a 1-nitro-3-substituted-3-amino-2-propanol diastereomer represented by Structural Formula I:

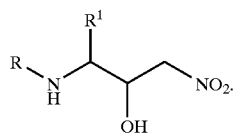

I

In Structural Formula I, R is an amine protecting group, and $R^1$ is an amino acid side-chain, a protected amino acid side-chain, substituted or unsubstituted aliphatic group, a substituted or unsubstituted aromatic group, a substituted or unsubstituted heteroaromatic group, a substituted or unsubstituted aralkyl or a substituted or unsubstituted heteroaralkyl group. Preferably, $R^1$ is an amino acid side-chain, a protected amino acid side-chain or an aromatic group. More preferably $R^1$ is an amino acid side-chain or a protected amino acid side-chain. The method involves contacting a 1-nitro-3-substituted-3-amino-2-propanone with a reducing agent to form a mixture of 1-nitro-3-substituted-3-amino-2-propanol diastereomers. The 1-nitro-3-substituted-3-amino-2-propanol diastereomers are then separated by simulated moving bed chromatography to obtain one or more 1-nitro-3-substituted-3-amino-2-propanol diastereomer.

In another embodiment, the method of preparing a 1-nitro-3-substituted-3-amino-2-propanol diastereomer represented by Structural Formula I involves contacting an amino acid having a protected amine group with a carboxylic acid activator to form an activated amino acid. The activated amino acid is contacted with a nitromethane anion solution to form a reaction mixture. An acid is added to the reaction mixture to form a 1-nitro-3-substituted-3-amino-2-propanone. The 1-nitro-3-substituted-3-amino-2-propanone is contacted with a reducing agent to form a mixture of 1-nitro-3-substituted-3-amino-2-propanol diastereomers which are separated by simulated moving bed chromatography to obtain one or more 1-nitro-3-substituted-3-amino-2-propanol diastereomer.

Another embodiment of the invention is a method of preparing a 1-nitro-3-benzyl-3-amino-2-propanol diastereomer represented by Structural Formula II:

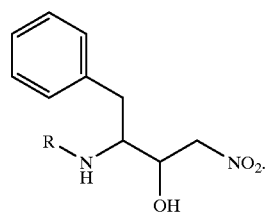

II

In Structural Formula II, R is an amine protecting group. The method involves contacting a phenylalanine that has a protected amine group with a carboxylic acid activator to form an activated phenylalanine. The activated phenylalanine is contacted with a nitromethane anion solution to form a reaction mixture. An acid is added to the reaction mixture to form a 1-nitro-3-benzyl-3-amino-2-propanone. The 1-nitro-3-benzyl-3-amino-2-propanone is contacted with a reducing agent to form a mixture of 1-nitro-3-benzyl-3-amino-2-propanol diastereomers which are separated by simulated moving bed chromatography to obtain one or more 1-nitro-3-benzyl-3-amino-2-propanol diastereomer.

Another embodiment of the invention is a method of preparing a diastereomer of a 3-substituted-3-amino-2- hydroxypropanoic acid salt represented by Structural Formula III:

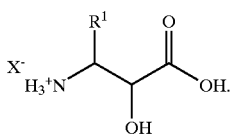

In Structural Formula III, $R^1$ is as defined in Structural Formula I. $X^-$ is $Cl^-$, $Br^-$, $F^-$, $I^-$, $^-HSO_4$, or $^-H_2PO_4$. The method involves contacting a mixture of 1-nitro-3-substituted-3-amino-2-propanol diastereomers with an acid to form a mixture of 3-substituted-3-amino-2-hydroxypropanic acid diastereomeric salts. The 3-substituted-3-amino-2-hydroxypropanic acid diastereomeric salts are then separated by simulated moving bed chromatography to obtain one or more 3-substituted-3-amino-2-hydroxypropanoic diastereomeric salt.

The method of the invention allows one or more 1-nitro-3-substituted-3-amino-2-propanol diastereomer or 3-substituted-3-amino-2-hydroxypropanoic acid salt to be obtained in high diastereomeric excess. The present method avoids the use of costly chiral reagents, and in contrast to the use of chiral reagents or selective recrystallization, more than one diasteromers can be collected in high diastereomeric excess without additional processing steps. In addition, the diastereomers obtained from simulated moving bed separation are more concentrated than those obtained using standard chromatographic techniques.

BRIEF DESCRIPTION OF THE DRAWINGS

FIG. 2B is a chromatogram showing the separation of two diastereomers of 1-nitro-3-benzyl-3-(N-ethoxycarbonyl)amino-2-propanol on a reverse phase C-18 column using a 40% acetonitrile/60% water (volume/volume) mobile phase.

DETAILED DESCRIPTION OF THE INVENTION

Figure 1:
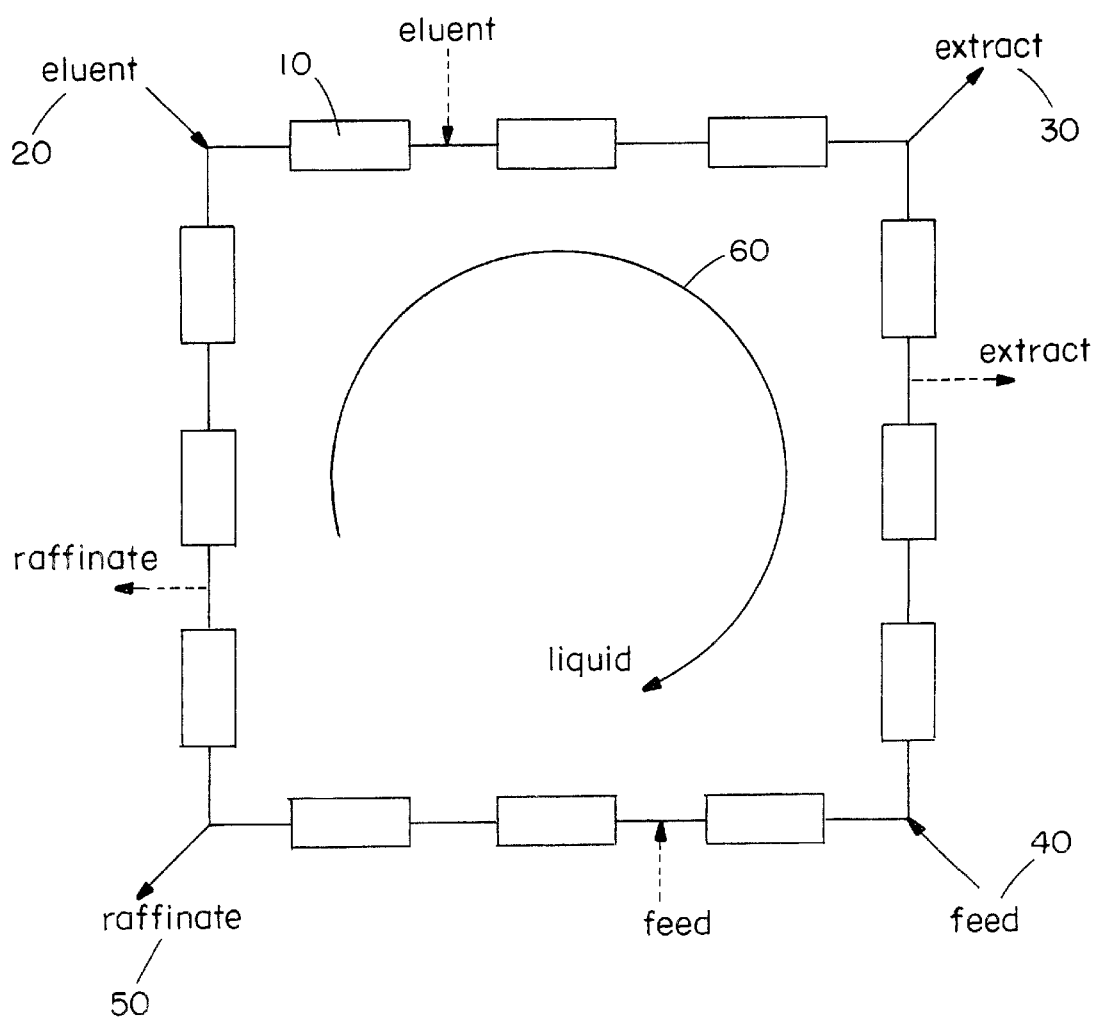
FIG. 1 is a schematic diagram of simulated moving bed chromatographic system having twelve columns.
Figure 2A:
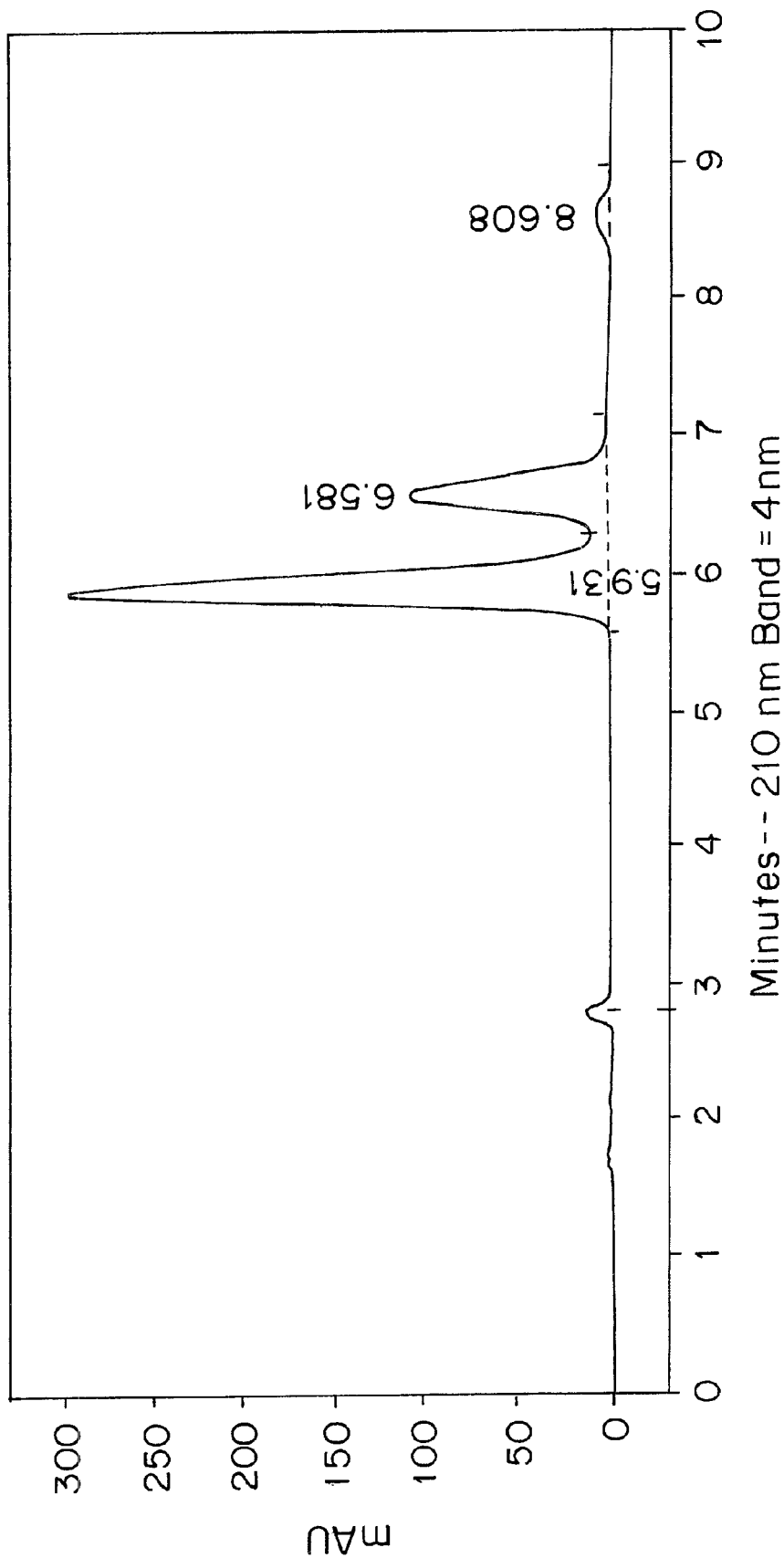
FIG. 2A is a chromatogram showing the separation of two diastereomers of 1-nitro-3-benzyl-3-(N-ethoxycarbonyl)amino-2-propanol on a reverse phase C-18 column using a 60% methanol/40% water (volume/volume) mobile phase.
Figure 3A:
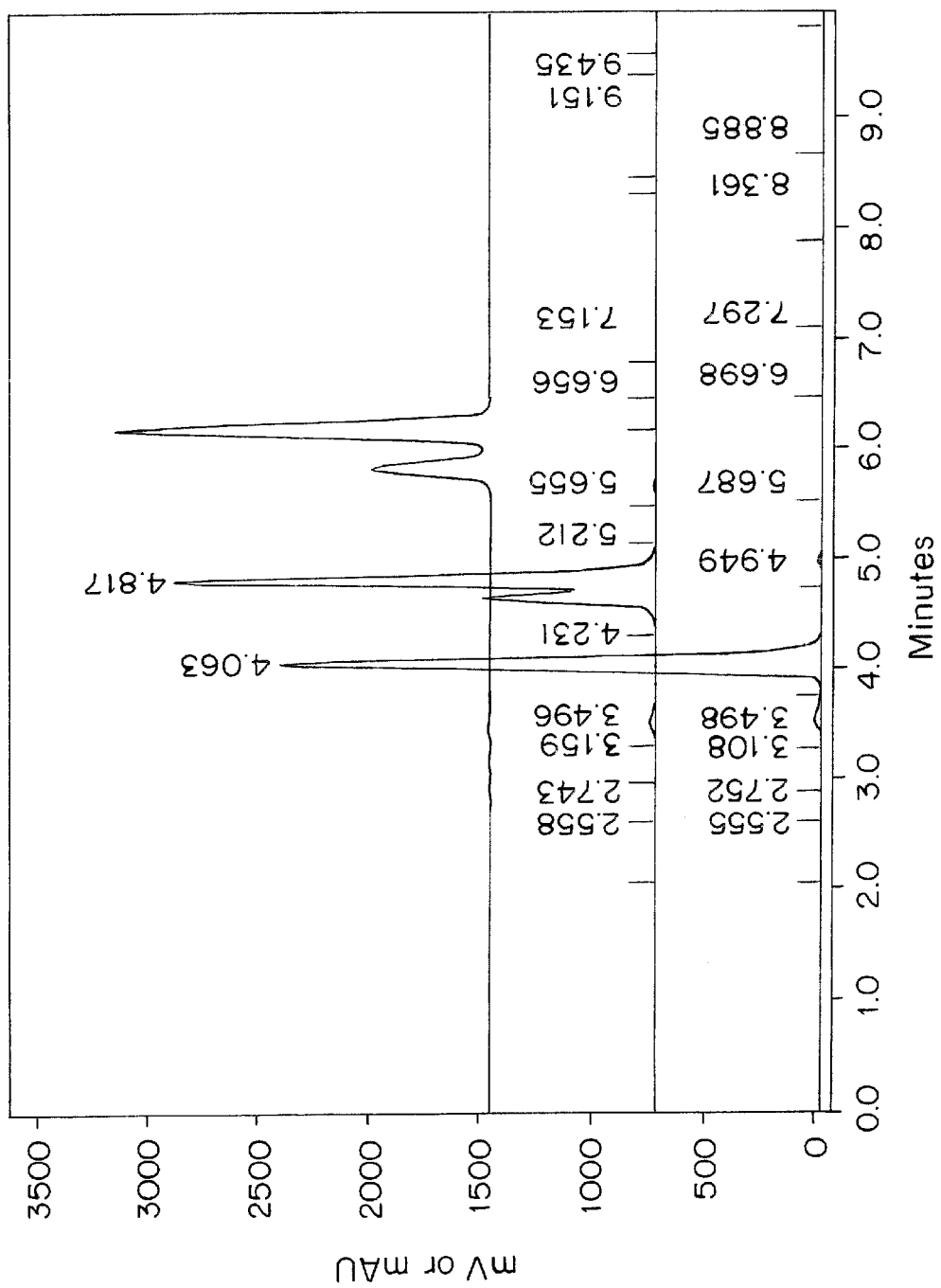
FIG. 3A is a series of three chromatograms showing the separation of two diastereomers of 1-nitro-3-benzyl-3-(N-ethoxycarbonyl)amino-2-propanol on a normal phase silica column using a 60% heptane/40% ethanol (volume/volume) mobile phase, a 70% heptane/30% ethanol (volume/volume) mobile phase and a 80% heptane/20% ethanol (volume/volume) mobile phase.
Figure 3B:
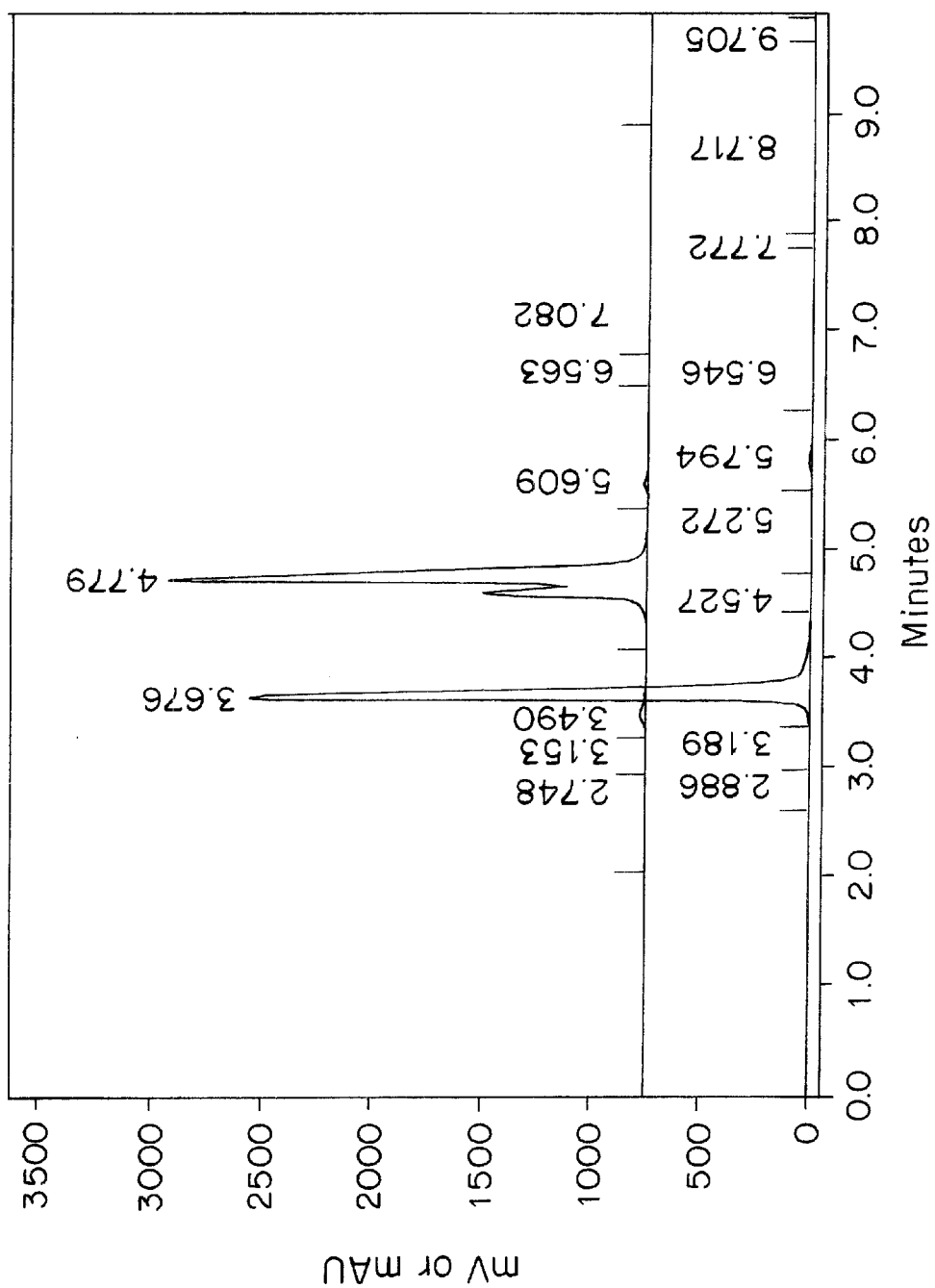
FIG. 3B is a series of two chromatograms showing the separation of two diastereomers of 1-nitro-3-benzyl-3-(N-ethoxycarbonyl)amino-2-propanol on a normal phase silica column using a 60% heptane/40% isopropanol (volume/volume) mobile phase and a 70% heptane/30% isopropanol (volume/volume) mobile phase.
Figure 3C:
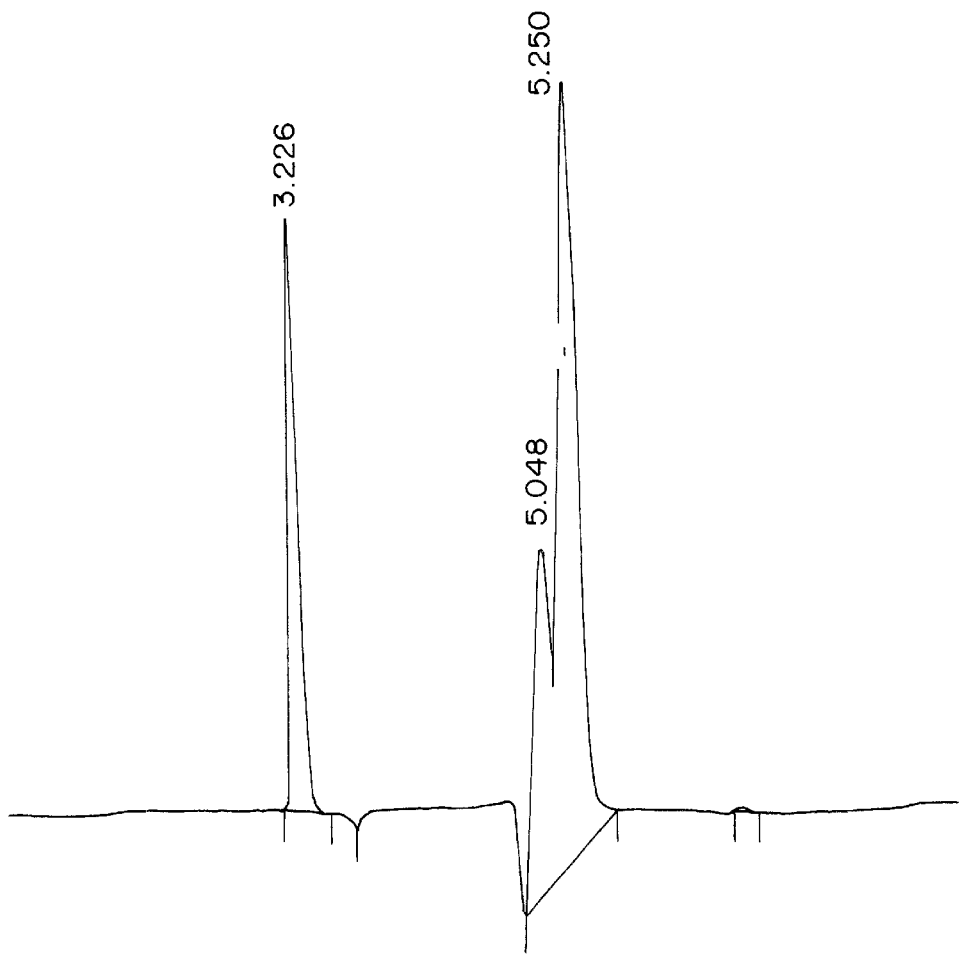
FIG. 3C is a chromatogram showing the separation of two diastereomers of 1-nitro-3-benzyl-3-(N-ethoxycarbonyl)amino-2-propanol on a normal phase silica column using a 60% heptane/40% tetrahydrofuran (THF) (volume/volume) mobile phase.
Figure 3D:
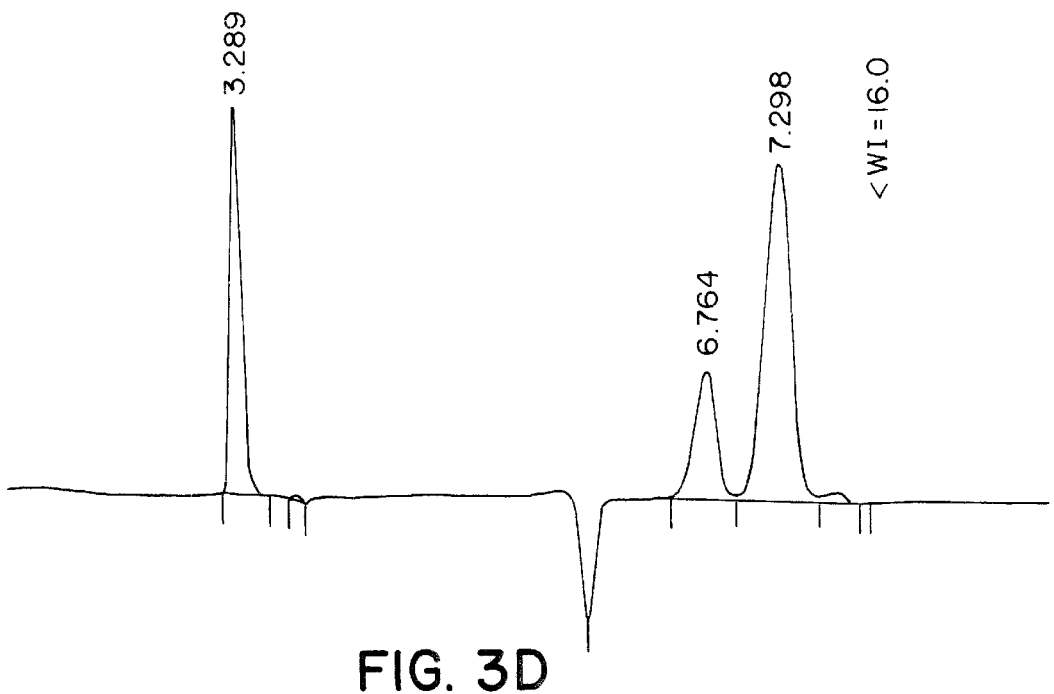
FIG. 3D is a chromatogram showing the separation of two diastereomers of 1-nitro-3-benzyl-3-(N-ethoxycarbonyl)amino-2-propanol on a normal phase silica column using a 70% heptane/30% THF (volume/volume) mobile phase.
Figure 4A:
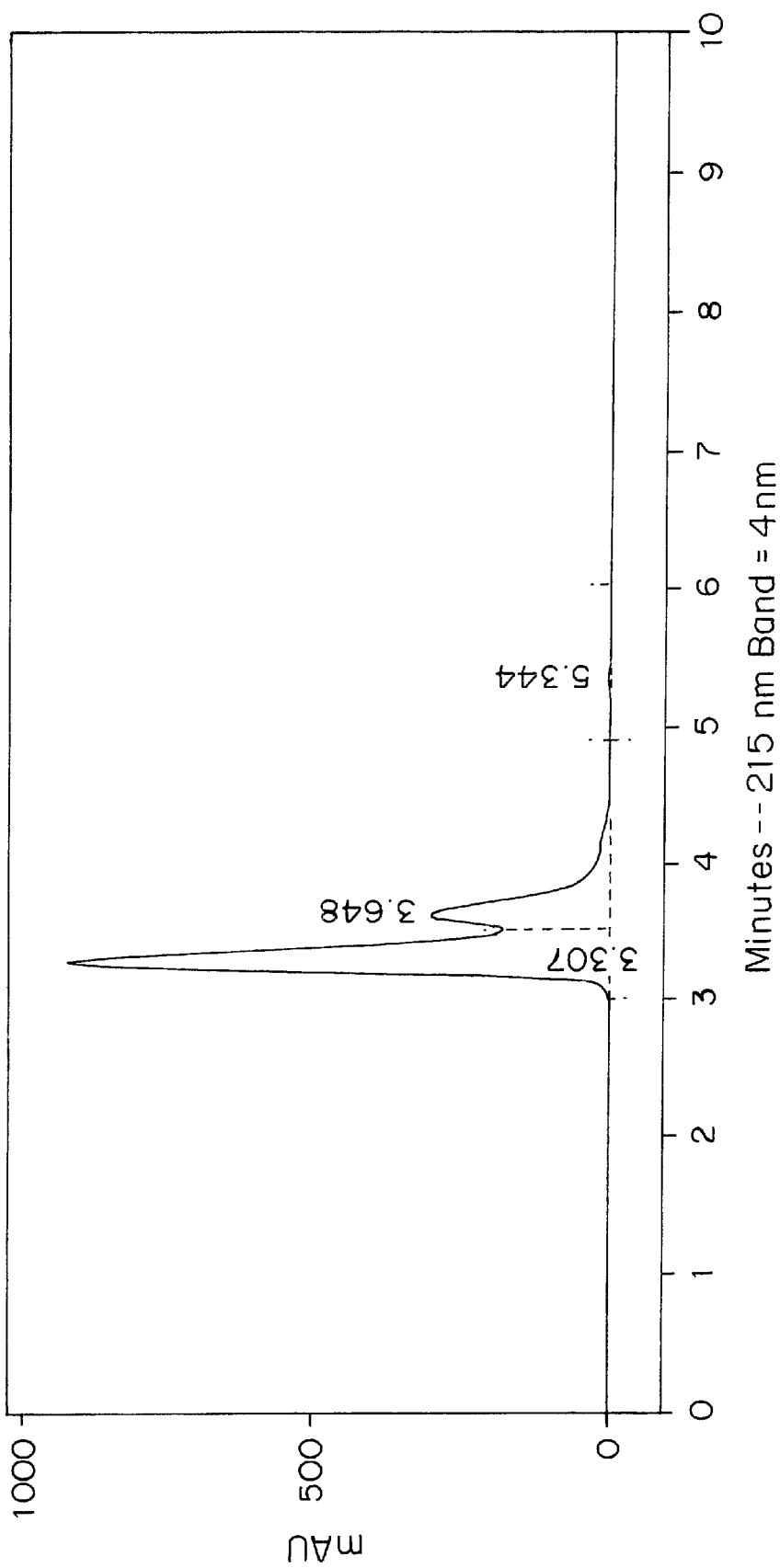
FIG. 4A is a chromatogram showing the separation of two diastereomers of 1-nitro-3-benzyl-3-(N-ethoxycarbonyl)amino-2-propanol on a divinyl benzene column using 100% methanol as the mobile phase.
Figure 4B:
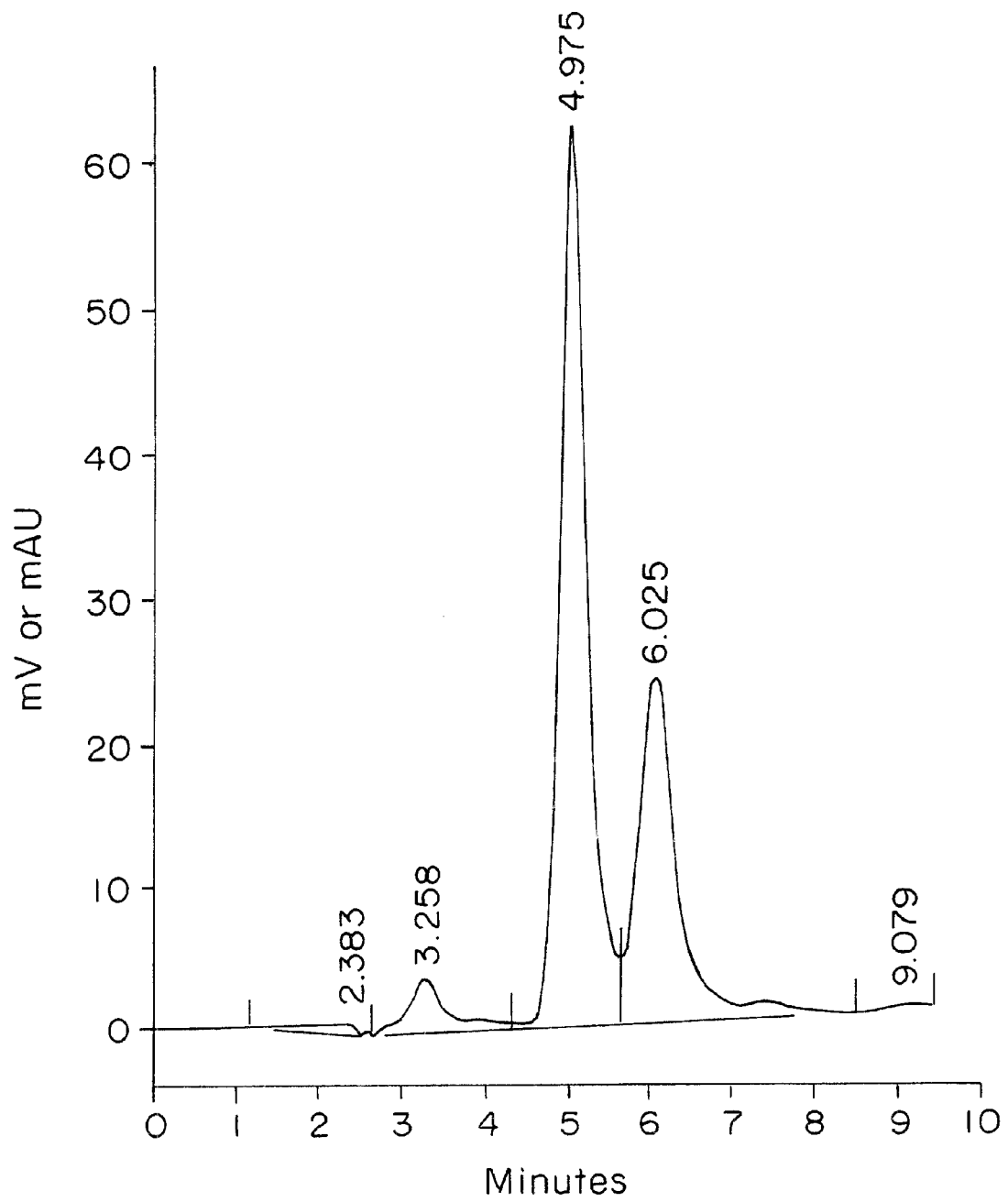
FIG. 4B is a chromatogram showing the separation of two diastereomers of 1-nitro-3-benzyl-3-(N-ethoxycarbonyl)amino-2-propanol on a divinyl benzene column using 90% methanol/10% water (volume/volume) mobile phase.

The features and other details of the method on the invention will now be more particularly described and pointed out in the claims. It will be understood that the particular embodiments of the invention are shown by way of illustration and not as limitations of the invention. The principle features of this invention can be employed in various embodiments without departing from the scope of the invention. All parts and percentages are by weight unless otherwise specified.

"Aliphatic groups" include straight chained, branched C1–C8, or cyclic C3–C8 hydrocarbons which are completely saturated or which contain one or more units of unsaturation. In one example, an aliphatic group is a C1–C4 alkyl group.

"Aromatic groups" include carbocyclic ring systems (e.g. benzyl) and fused polycyclic, carbocyclic ring systems (e.g. naphthyl, anthracenyl and 1,2,3,4-tetrahydronaphthyl).

"Heteroaromatic groups", as used herein, include heteroaryl ring systems (e.g., thienyl, pyridyl, pyrazole, isoxazolyl, thiadiazolyl, oxadiazolyl, indazolyl, furans, pyrroles, imidazoles, pyrazoles, triazoles, pyrimidines, pyrazines, thiazoles, isoxazoles, isothiazoles, tetrazoles, or oxadiazoles) and heteroaryl ring systems in which a carbocyclic aromatic ring, carbocyclic non-aromatic ring or heteroaryl ring is fused to one or more other heteroaryl rings (e.g., benzo(b)thienyl, benzimidazole, indole, tetrahydroindole, azaindole, indazole, quinoline, imidazopyridine, purine, pyrrolo[2,3-d]pyrimidine, and pyrazolo[3,4-d]pyrimidine).

An "aralkyl group", as used herein, is an aromatic group that is linked to a compound by an aliphatic group having from one to about six carbon atoms.

An "heteroaralkyl group", as used herein, is a heteroaromatic group that is linked to a compound by an aliphatic group having from one to about six carbon atoms.

Suitable substituents for an aliphatic group, an aromatic group, a heteroaromatic group, an aralkyl group and a heteroaralky group are those which are compatible with the disclosed reactions, i.e., do not significantly reduce the yield of the reactions and do not cause a significant amount of side reactions. Suitable substituents generally include aliphatic groups, substituted aliphatic groups, aryl groups, halogens, halogenated alkyl groups (e.g., trihalomethyl), nitro, nitrile, $-CONHR^2$, $-CONR^2R^3$, $-OR^2$, $-SR^2$, $-S(O)R^2$, $-S(O)_2R^2$, wherein $R^2$ and $R^3$ are each, independently, an aliphatic group, or an aryl group. Although certain functional groups may not be compatible with one or more of the disclosed reactions, these functional groups may be present in a protected form. The protecting group can then be removed to regenerate the original functional group. The skilled artisan will be able to select, using no more than routine experimentation, protecting groups which are compatible with the disclosed reactions.

An "amino acid" is a compound represented by $NH_2$—$CHR^4$—COOH, wherein $R^4$ is an amino acid side-chain or a protected amino acid side-chain. An amino acid side-chain can be an aliphatic group, a substituted aliphatic group, an aromatic group or a substituted aromatic group. A "naturally-occurring amino acid" is an amino acid found in nature. In naturally-occurring amino acids, $R^4$ can also be —H. When $R^4$ is —H it is not an amino acid side-chain as used herein. Examples of naturally occurring amino acids include alanine, valine, leucine, isoleucine, aspartic acid, glutamic acid, serine, threonine, glutamine, asparagine, arginine, lysine, ornithine, proline, hydroxyproline, phenylalanine, tyrosine, tryptophan, cysteine, methionine and histidine. Examples of naturally occurring amino acid side-chains include methyl (alanine), isopropyl (valine), sec-butyl (isoleucine), —$CH_2CH$(—$CH_3)_2$ (leucine), benzyl (phenylalanine), p-hydroxybenzyl (tyrosine), —$CH_2OH$ (serine), —$CHOHCH_3$ (threonine), —$CH_2$-3-indoyl (tryptophan), —$CH_2COOH$ (aspartic acid), —$CH_2CH_2COOH$ (glutamic acid), —$CH_2C(O)NH_2$ (asparagine), —$CH_2CH_2C(O)NH_2$ (glutamine), —$CH_2SH$ (cysteine), —$CH_2CH_2SCH_3$ (methionine), —$(CH_2)_4NH_2$ (lysine), —$(CH_2)_3NH_2$ (ornithine), —$[(CH)_2]_4NHC(=NH)NH_2$ (arginine) and —$CH_2$-3-imidazoyl (histidine).

The side-chains of alanine, valine, leucine and isoleucine are aliphatic, i.e., they contain only carbon and hydrogen, and are each referred to herein as "the aliphatic side-chain of a naturally occurring amino acid."

The side-chains of other naturally-occurring amino acids comprise a heteroatom-containing functional group, e.g., an alcohol (serine, tyrosine, hydroxyproline and threonine), an amine (lysine, ornithine, histidine and arginine), a thiol (cysteine) or a carboxylic acid (aspartic acid and glutamic acid). When the heteroatom-containing functional group is modified to include a protecting group, the side-chain is referred to as the "protected side-chain" of an amino acid.

The selection of a suitable protecting group depends upon the functional group being protected, the conditions to which the protecting group is being exposed and to other functional groups which may be present in the molecule. Suitable protecting groups for the functional groups discussed above are described in Greene and Wuts, "Protective Groups in Organic Synthesis," John Wiley & Sons (1991), the entire teachings of which are incorporated into this application by reference. The skilled artisan can select, using no more than routine experimentation, suitable protecting groups for use in the disclosed synthesis, including protecting groups other than those described below, as well as conditions for applying and removing the protecting groups.

Examples of suitable alcohol protecting groups include benzyl, allyl, trimethylsilyl, tert-butyldimethylsilyl, acetate, and the like. Benzyl is a preferred alcohol protecting group.

Examples of suitable amine protecting groups include benzyloxycarbonyl, tert-butoxycarbonyl, tert-butyl, benzyl and fluorenylmethyloxycarbonyl (Fmoc). Carbamate protecting groups, such as tert-butoxycarbonyl and ethyloxycarbonyl, are preferred amine protecting groups.

Examples of suitable carboxylic acid protecting groups include tert-butyl, Fmoc, methyl, methoxylmethyl, trimethylsilyl, benzyloxymethyl, tert-butyldimethylsilyl and the like. Tert-butyl is a preferred carboxylic acid protecting group.

Examples of suitable thiol protecting groups include S-benzyl, S-tert-butyl, S-acetyl, S-methoxymethyl and the like.

Lysine, aspartate and threonine are examples of amino acid side-chains that are preferably protected. The following structures are examples of a protected lysine side-chain, a protected aspartate side-chain and a protected threonine side-chain, respectively:

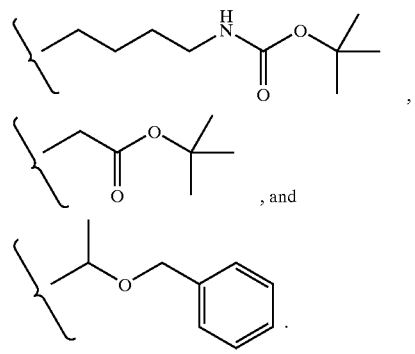

As used herein, in the chemical name 1-nitro-3-substituted-3-amino-2-propanol, 1-nitro-3-substituted-3-amino-propanone or 1,3-diamino-3-substituted-2-propanol, the 3-amino group can be a protected or unprotected amine group.

In one embodiment of the invention, two or more diastereomers of 1-nitro-3-substituted-3-amino-2-propanol, represented by Structural Formula I, are formed by contacting a 1-nitro-3-substituted-3-amino-2-propanone with a carbonyl reducing agent in a solution. The 1-nitro-3-substituted-3-amino-2-propanone can be represented by Structural Formula IV:

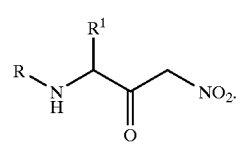

IV

In Structural Formula IV, R and $R^1$ are defined as for Structural Formula I. The amount of the carbonyl reducing agent used is an amount which will reduce and hydrogneate at least a portion of the 1-nitro-3-substituted-3-amino-2-propanone. Typically, from about 0.1 moles to about 100 moles of a carbonyl reducing agent are used per mole of 1-nitro-3-substituted-3-amino-2-propanone.

A carbonyl reducing agent, suitable for the method of this invention, is a chemical or combination of chemicals which will react with a 1-nitro-3-substituted-3-amino-2-propanone to reduce and hydrogenate the carbonyl group, but will generally not affect the nitro group. Suitable carbonyl reducing agents include, for instance, sodium borohydride, lithium borohydride, borane, disiamylborane, 9-borabicyclo[3.3.1]nonane, lithium tri-tert-butoxy-aluminohydride, lithium triethylborohydride and lithium tri(sec-butyl) borohydride.

Suitable solvents for the solution include organic solvents, such as alcohols, esters, ethers, including cyclic ethers, such as tetrahydrofuran.

It is understood that the 1-nitro-3-substituted-3-amino-2-propanone, the carbonyl reducing agent and the solvent may be combined concurrently, sequentially, or in any order or combination. It is also understood that the 1-nitro-3-substituted-3-amino-2-propanone may be added as a solid or in solution, and that the carbonyl reducing agent may be added as a solid, liquid, in solution, or any combination thereof.

After the reduction is allowed to proceed for about 0.5 hours to about 24 hours, the reaction mixture is acidified with a suitable aqueous acid. Suitable acids are those acids which will acidify the salt of the 1-nitro-3-substituted-3-amino-2-propanol compound, but not cleave the amine protecting group. Suitable acids include, for example, $KHSO_4$, ammonium chloride and citric acid.

In 1-nitro-3-substituted-3-amino-2-propanone, the third carbon of the propanone backbone is a chiral center. Therefore, the 1-nitro-3-substituted-3-amino-2-propanone, which is contacted with the reducing agent, can be a 3S or 3R enantiomer or a mixture of enantiomers. When the 1-nitro-3-substituted-3-amino-2-propanone is either a 2S or 2R enantiomer, two diastereomers are formed when the carbonyl is reduced.

Once formed, the diastereomers of 1-nitro-3-substituted-3-amino-2-propanol are separated by simulated moving bed chromatography. Simulated moving bed chromatography is similar in principal to counter-current chromatography. In conventional one-dimensional chromatography using a solid stationary phase and a liquid mobile phase, two compounds are separated based on their different affinities for the solid phase. The compound that has a higher affinity for the stationary solid phase will stay absorbed and, thus, stationary longer than the compound which has less affinity for the stationary phase. Since the compound that has less affinity for the stationary phase will spend more time in the liquid mobile phase, it will move down the column away from the other compound. In counter-current chromatography, the solid phase is not stationary. It moves in the opposite direction as the mobile phase. Thus, the flow rate of the solid and liquid phases can be set up so that the two compounds being separated migrate in opposite directions. If the mixture of the two compounds enters the column through a feed in the center of the column, the separated compounds can each be collected at opposite ends of the column through the extract line, which contains the less absorptive compound, and the raffinate line, which contains the more absorptive compound. In counter-current chromatography, the column can be loaded more highly with sample to be separated than in standard chromatography. Therefore, it is useful for large scale separations. However, actual movement of the solid phase is difficult to achieve without mixing of the compounds being separated.

In simulated moving bed chromatography, a number of columns (10) are connected in a continuous series (see FIG. 1). The flow of the solid phase is simulated by moving the eluent (20), extract (30), feed (40) and raffinate (50) lines one column forward in the direction of the fluid flow (60) at fixed intervals. This system allows for continuous feed of a mixture of compounds to be separated and continuous elution of separated product. Simulated moving bed chromatography can also be used to separate more than two compounds. Simulating bed chromatography has been described in more detail in U.S. Pat. No. 2,985,589, the teachings of which are incorporated herein in their entirety.

A feature of the present invention is the adjustment of simulated moving bed separation conditions to obtain at least one 1-nitro-3-substituted-3-amino-2-propanol diastereomer in 95% diastereomeric excess. For a pair of diastereomers, diastereomeric excess of diastereomer D1 in relation to diastereomer D2 can be calculated using Equation (1):

$$\% \text{ diastereomeric excess} = \frac{(D1 - D2)}{(D1 + D2)} \times 100 \quad (1)$$

In Formula (1), D1 and D2 are relative amounts of each diastereomer. The relative amount of each diastereomer can be determined by HPLC or other techniques known to those skilled in the art.

After separating the 1-nitro-3-substituted-3-amino-2-propanol diastereomers by simulated moving bed chromatography, one or more diastereomers are recovered in at least 95% diastereomeric excess. In the case where two diastereomers are separated, both can be recovered in 95% diastereomeric excess.

A 1-nitro-3-substituted-3-amino-2-propanol diastereomer, which has been recovered in at least 95% diastereomeric excess, can be contacted with a nitro reducing agent under conditions which maintains the diastereomeric excess of the diastereomer to form a 1,3-diamino-3-substituted-2-propanol diastereomer in about 90% to about 95% diastereomeric excess.

1,3-diamino-3-substituted-2-propanol diastereomers can be represented by Structural Formula V:

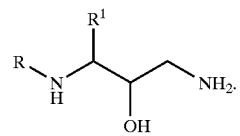

In Structural Formula V, R and $R^1$ are defined as for Structural Formula I.

The 1-nitro-3-substituted-3-amino-2-propanol diastereomer is combined with the nitro reducing agent in a solvent to form a reaction mixture. The diastereomeric excess of the 1-nitro-3-substituted-3-amino-2-propanol is typically maintained under the conditions described below.

In a preferred embodiment, the nitro reducing agent comprises a hydrogen source in the presence of a hydrogenation catalyst. Suitable hydrogen sources include, for instance, formic acid, soluble formic acid salts, such as ammonium formate, tetrahydronaphthalene and hydrogen. The amount of the hydrogen source used is an amount which will reduce and hydrogenate at least a portion of the 1-nitro-3-substituted-3-amino-2-propanol diastereomer. Typically, the amount of the hydrogen source used is from about 0.1 molar equivalents to about 100 molar equivalents per mole of the 1-nitro-3-substituted-3-amino-2-propanol diastereomer.

Hydrogenation catalysts suitable for reducing the nitro group include, for example, palladium on charcoal, palladium hydroxide, platinum black, platinum oxide, a combination of sodium borohydride and nickel chloride, Raney nickel, or a combination of sodium borohydride and cobalt chloride. The amount of catalyst used is typically from about 0.05 molar equivalents to about 10 molar equivalents per mole of the 1-nitro-3-substituted-3-amino-2-propanol diastereomer.

Suitable solvents in which the nitro reduction can be carried out include organic solvents, such as alcohols, alkanes, benzene, ethers, toluene, tetrahydrofuran, or any combination thereof. The reaction mixture is maintained between about −40° C. and the reflux temperature of the solvent. Preferably, the reaction temperature is from about 20° C. to about 30° C.

In another embodiment, the nitro reducing agent, suitable for the method of the invention, is a chemical or combination of chemicals which will react to reduce and hydrogenate the nitro group to form an amino group. Suitable nitro reducing agents of this type include, for instance, lithium aluminum hydride. The amount of the nitro reducing agent used is an amount which will reduce and hydrogenate at least a portion of the 1-nitro-3-substituted-3-amino-2-propanol. Typically, from about 0.1 moles to about 100 moles of nitro reducing agent are used per mole of 1-nitro-3-substituted-3-amino-2-propanol.

It is understood that the 1-nitro-3-substituted-3-amino-2-propanol, the nitro reducing agent and the solvent may be combined concurrently, sequentially, or in any order or combination. It is also understood that the 1-nitro-3-substituted-3-amino-2-propanol may be added as a solid or in solution. In addition, the nitro reducing agent may be added as a solid, liquid, gas, slurry, solution or combination thereof.

When only one diastereomer is a desirable product, the desired diastereomer, designated the first diastereomer, can be recovered in 95% diastereomeric excess and a second diastereomer or a mixture of the first 1-nitro-3-substituted-3-amino-2-propanol diastereomer and the second 1-nitro-3-substituted-3-amino-2-propanol diastereomer can be recovered and converted into the desired product. The recovered second diastereomer or mixture of the second diastereomer and first diastereomer can be contacted with an oxidizing agent to form 1-nitro-3-substituted-3-amino-2-propanone. Any oxidizing agent can be used which will oxidize a secondary alcohol to a ketone without reacting with any other part of the 1-nitro-3-substituted-3-amino-2-propanol. Strong oxidizing agents, such as $CrO_3$, $KMnO_4$, $Br_2$, $MnO_2$, ruthenium tetroxide, can be used. Jone's reagent (a solution of chromic acid and sulfuric acid) can be used to oxidize a 1-nitro-3-substituted-3-amino-2-propanol which are not acid sensitive. When less acidic conditions are necessary, Collin's reagent (dipyridine Cr(VI) oxide), Corey's reagent (pyridinium chlorochromate), or pyridinium dichromate can be used. For acid sensitive compounds, the oxidation can be carried out using $CrO_3$ in hexamethylphosphorous triamide. Alternatively, a chemoselective oxidizing agents, such as a N-halosuccinimide, can be used.

The 1-nitro-3-substituted-3-amino-2-propanone is contacted with a reducing agent to form a mixture of the first and the second 1-nitro-3-substituted-3-amino-2-propanol diastereomers that contains a higher diastereomeric excess of the first diastereomer than was present before the oxidation step. This mixture can then be separated by simulated moving bed chromatography to obtain the desired 1-nitro-3-substituted-3-amino-2-propanol diastereomer in at least 95% enantiomeric excess. This cycle of oxidation, reduction and separation can be repeated until the desired 1-nitro-3-substituted-3-amino-2-propanol diastereomer has been obtained in about 85% yield, preferably in about 90% yield. Alternatively, the cycle of oxidation, reduction and separation can be repeated until less than 10%, preferably, less than 5% of the undesired diastereomer remains unconverted into the desired diastereomer.

Another embodiment of the present invention is a method of preparing a 1-nitro-3-substituted-3-amino-2-propanol represented by Structural Formula I from an amino acid starting material. The amine group of the amino acid starting material is typically protected so that it will not participate in unwanted side reactions. The amino acid can be a D-isomer or an L-isomer or a mixture of both. Preferably, the amino acid is a D-isomer or an L-isomer.

The protected amino acid is contacted with a carboxylic acid activator which converts the amino acid into an activated amino acid. Typically, the reaction to form the activated amino acid is carried out in an aprotic solvent under anhydrous conditions. Carboxylic acid activators are compounds that react with a carboxylic acid to displace the hydroxyl group of the carboxylic acid with a radical suitable to make the carbonyl carbon of said carboxylic acid group more susceptible to nucleophilic addition. Examples of suitable carboxylic acid activators include N-hydroxysuccinimide, p-nitrophenol, 1,1'-carbonyldiimidazole, isobutyl chloroformate, dimethylaminopropylethylcarbodiimide (EDC), dicyclohexyl carbodiimide (DCC) and 1-hydroxybenzotriazole.

Suitable solvents for the reaction include methylene chloride, dimethylformamide, tetrahydrofuran, dichloroethane and diethyl ether.

It is understood that the amino acid, the carboxylic acid activator and the solvent may be combined concurrently, sequentially, or in any order or combination. It is also understood that the amino acid may be added as a solid or in solution. It is further understood that the carboxylic acid activator may be added as a solid, liquid or in solution.

Generally, from about 0.1 moles to about 10 moles of an carboxylic acid activator are used per mole of amino acid. A preferred range is from about 1 mole to about 1.5 moles of carboxylic acid activator per mole of amino acid.

In one embodiment, the amino acid and carboxylic acid activator are refluxed to drive the reaction to completion. Typically, refluxing is performed for about 0.5 hours to about 4 hours, or until gas evolution subsides.

The activated amino acid is then contacted with a nitromethane anion solution under anhydrous conditions to form a reaction mixture, and subsequently the reaction mixture is acidified to form a 1-nitro-3-substituted-3-amino-2-propanone.

The nitromethane anion solution is formed under anhydrous conditions by mixing an anhydrous base with nitromethane, and optionally an aprotic solvent, such as tetrahydrofuran. As the formation of the nitromethane anion solution is typically exothermic, and as salts of nitromethane can be unstable and possibly explosive at higher temperatures, the temperature of the nitromethane anion solution is typically maintained at a cold temperature, such as about 5° C. or less.

Suitable bases are those which will deprotonate the nitromethane compound to form a nitromethane anion. Examples of suitable anhydrous bases include metal alkoxides, such as potassium t-butoxide and sodium methoxide, sodium hydride, sodium bicarbonate and lithium diisopropylamide. The amount of the anhydrous base used is that amount which will deprotonate at least a portion of the nitromethane molecules to form nitromethane anions. Typically, from about 0.1 moles to about 1000 moles of anhydrous base per mole of nitromethane compound.

Acids suitable to acidify the reaction mixture to form the 1-nitro-3-substituted-3-amino-2-propanone consist of acids which will reduce pH to a sufficiently low value to prevent significant enolate formation and to react with any remaining nitromethane anions, but will generally not cleave the protecting groups from the amine or the side-chain of the amino acid. Typically, pH is reduced to about 5 or less, with a pH of 2–5 preferred. Suitable acids include, for instance, $H_2S_4$, HCl, HBr, $H_3PO_4$, $KHSO_4$, citric acid, acetic acid and combinations thereof. When the protecting group is a ethyloxycarbonyl or a tert-butoxycarbonyl, the pH preferably is above 3. Therefore, mild acids, such as $KHSO_4$ are preferred.

The 1-nitro-3-substituted-3-amino-2-propanone is then contacted with a carbonyl reducing agent to form a mixture of 1-nitro-3-substituted-3-amino-2-propanol diastereomers which are separated by simulated moving bed chromatography.

Another embodiment of the invention is a method of preparing a 1-nitro-3-benzyl-3-amino-2-propanol represented by Structural Formula II. The method involves contacting a phenylalanine having a protected amine group with a carboxylic acid activator to form an activated amino acid. The activated amino acid is contacted with a nitromethane anion solution to form a reaction mixture which is acidified to form a 1-nitro-3-benzyl-3-amino-2-propanone. The 1-nitro-3-benzyl-3-amino-2-propanone is contacted with a reducing agent to form a mixture of 1-nitro-3-benzyl-3-amino-2-propanol diastereomers which can be separated by simulated moving bed chromatography.

In a further embodiment of the invention, a mixture of 1-nitro-3-substituted-3-amino-2-propanol diastereomers is converted into a mixture of 3-substituted-3-amino-2-hydroxypropanoic acid diastereomeric salts represented by Structural Formula III. The 3-substituted-3-amino-2-hydroxypropanoic acid diastereomeric salts are then separated by simulated moving bed chromatography. Alternatively, the 1-nitro-3-substituted-3-amino-2-propanol diastereomers can be separated via simulated moving bed chromatography, then one or both of the separated diastereomers can be individually converted to a 3-substituted-3-amino-2-hydroxypropanoic acid salt under conditions in which the stereochemistry of the chiral centers is maintained. The 3-amine group of the 1-nitro-3-substituted-3-amino-2-propanol diastereomers can be protected with an acid labile protecting group, such as a carbamate protecting group, or unprotected. The reaction involves heating either a mixture of 1-nitro-3-substituted-3-amino-2-propanol diastereomers or a 1-nitro-3-substituted-3-amino-2-propanol diastereomer which has been separated via simulated moving bed chromatography with a strong acid, such as HCl, HBr, Hl, HF, $H_3PO_4$, or $H_2SO_4$ for about 10 hours to about 30 hours. The reaction temperature is typically about 80° C. to about 120° C.

EXAMPLES

Example 1

Synthesis of 1-Nitro-3-Benzyl-3-(N-Ethoxycarbonyl)amino-2-Propanone

Potassium t-butoxide was added to 40 ml anhydrous THF a 250 ml round-bottom with overhead stirrer. After the solid went into solution, the solution, was cooled to 1.7° C. in an ice water brine bath. Nitromethane was added to this mixture, and a white precipitate formed. The temperature was maintained at less than 10° C.

In a separate flash flushed with argon, N-(ethoxycarbonyl) phenylalanine was dissolved in 40 ml anhydrous THF with stirring. To this pale yellow solution, 3.76 g of 1,1'-carbonyldiimidazole was added in 3 portions. Each time the 1,1'-carbonyldiimidazole was added, effervescence was observed for several minutes after the addition. After the final addition, the solution was allowed to stir for 30 minutes.

The solution of the activated N-(ethoxycarbonyl) phenylalanine was added dropwise to the white nitromethane/potassium t-butoxide slurry. The temperature was kept below 10° C. Addition time was approximately 10 minutes.

The progress of the reaction was followed by thin layer chromatography (TLC) using a silica solid phase and a mobile phase composed of 10% methanol (volume/volume) in methylene chloride. After 2.5 hours, the reaction mixture was quenched with 30 mL 10% aqueous HCl to bring the pH to 3. The mixture was allowed to stir for 30 minutes at pH 3, then was concentrated under reduced pressure. After concentration, the residue was diluted with 10 mL of water, then extracted with 40 mL of ethyl acetate. The water layer was washed with 2×25 mL of ethyl acetate. Then the combined organic layers were washed with 2×10 ml water, dried over $MgSO_4$, and concentrated to yield 5.0 g of 1-nitro-3-benzyl-3-(N-ethoxycarbonyl)amino-2-propanone as a yellowish white solid.

Example 2

Synthesis of 1-Nitro-3-Benzyl-3-(N-Ethoxycarbonyl)amino-2-Propanol Diastereomers 5.75 g of 1-nitro-3-benzyl-3-(N-ethoxycarbonyl)amino-2-propanone was dissolved in 74 g of methanol, and then cooled to 0–5° C. Sodium borohydride (1–2 g) was slurried in 2.8 g water, then added slowly in portions over a 25 minute period to the 1-nitro-3-benzyl-3-(N-ethoxycarbonyl)amino-2-propanone solution. The temperature of the reaction mixture was maintained below 5° C. during the addition. The mixture was stirred at 0–5° C. for 30 minutes, then at room temperature for 45 min. 14 g 10% HCl was added to the mixture to bring the pH to 3, then allowed to stir for an additional 30 minutes.

The methanol was evaporated under reduced pressure and the solution was diluted with 40 g water and extracted with 35 g ethyl acetate. The aqueous layer was extracted with 2×20 g ethyl acetate. The combined organic layers were then washed with 4×20 g of an aqueous saturated $NaHCO_3$ solution and the ethyl acetate layer was concentrated under reduced pressure to yield 4.6 g of the 1-nitro-3-benzyl-3-(N-ethoxycarbonyl)amino-2-propanol diastereomers as a yellow solid.

Example 3

Determination of Simulated Moving Bed Separation Conditions for Separation of 1-Nitro-3-Benzyl-3-(Protected)amino-2-Propanol A. Solubility of 1-Nitro-3-Benzyl-3-(N-Ethoxycarbonyl) amino-2-Propanol Diastereomers In order to have a concentrated sample for loading on the simulated moving bed separation system, a high degree of solubility in the mobile phase to be used for the separation is desirable. Therefore, the solubility of the 1-nitro-3-benzyl-3-(N-ethoxycarbonyl)amino-2-propanol diastereomers in several solvent systems was determined. The results are presented in Table I.

TABLE I

Solubility of 1-nitro-3-benzyl-3-benzyl-3-(N-ethoxycarbonyl)amino-2-propanol diastereomers in various solvent systems.

| Mobile Phase | % Solubility |
| --- | --- |
| 100% THF | 16.57%, 37.24%, 41.18% |
| 50% heptane/50% THF | 20% |
| 70% heptane/30% THF | 4% |
| 80% heptane/20% ethanol | 0.31%, 1.86% |
| 70% heptane/30% ethanol | 20% |
| 70% heptane/30% isopropanol | 0.36% |

TABLE I-continued

Solubility of 1-nitro-3-benzyl-3-benzyl-3-(N-ethoxycarbonyl)amino-2-propanol diastereomers in various solvent systems.

| Mobile Phase | % Solubility |
|---|---|
| 40% water/60% methanol | 1.7% |
| 60% water/40% acetonitrile | 3.29% |
| 50% methanol/50% THF | 78% |
| 100% methanol | 40% |
| 80% toluene/20% THF | 6% |
| 10% ethyl acetate/90% methylene chloride | 3.8% |
| 70% heptane/30% ethyl acetate | 1.11%, 1.09%, 1.31% |
| 50% heptane/50% ethyl acetate | 3.81% |

B. Separation of 1-Nitro-3-Benzyl-3-(N-protected)amino-2-Propanol Diastereomers Using Conventional One-Dimensional High Pressure Liquid Chromatography (HPLC)

The separation of the 1-nitro-3-benzyl-3-(N-ethoxycarbonyl)amino-2-propanol diastereomers was done using several mobile phase systems and several reverse phase columns, normal phase columns and chiral columns. CHIRALPAK AD® and CHIRALPAK AS® columns were purchased from Chiral Technologies, Inc., Exton, Pa. CHIRALPAK AD® and CHIRALPAK AS® have a solid support with a chiral amylose derivative. CHIREX® 3001, CHIREX® 3014, CHIREX® 3022 and NUCLEOSIL® columns were purchased from Phenomenex, Inc., Torrance, Calif.

The results for 1-nitro-3-benzyl-3-(N-ethoxycarbonyl)amino-2-propanol diastereomers, 1-nitro-3-benzyl-3-(N-tert-butoxycarbonyl)amino-2-propanol diastereomers, and 1-nitro-3-benzyl-3-(N-phenylmethoxycarbonyl)amino-2-propanol diastereomers are summarized in Tables II, III and IV, respectively.

The solvent front was determined by measuring the void time using standard chromatographic techniques. For example, uracil was used as a tracer compound which eluted with the solvent front when the separation was done using a reverse phase C18 column. The capacity factors, $k_1'$ and $k_2'$ for each of the two diastereomers was determined for each column and mobile phase system using Equation (2):

$$k' = \frac{(\text{retention time}) - (\text{solvent front})}{(\text{solvent front})} \quad (2)$$

The selectivity constant, $\alpha$, for the system was calculated by taking the ratio of $k_2'$ to $k_1'$. A value of $\alpha$ of 1.15 or greater is necessary in order for separation of the diastereomers via simulated moving bed chromatography to be possible.

TABLE II

Analysis of the separation of 1-nitro-3-benzyl-3-(N-ethoxycarbonyl)amino-2-propanol diastereomers by conventional HPLC.

| Column Type | Length (mm) | Diameter (mm) | Particle size (μm) | Flow Rate (mL/min.) | Mobile Phase | $k_2'$ | α |
|---|---|---|---|---|---|---|---|
| C18 | 250 | 4.6 | 5 | 1 | 60% water/40% acetonitrile | 0.81 | 1.21 |
| C18 | 250 | 4.6 | 5 | 1 | 40% water/60% methanol | 2.66 | 1.16 |
| divinyl benzene | 100 | 10.0 | 5 | 2 | 100% methanol | 0.30 | 1.66 |
| silica | 250 | 4.6 | 5 | 1 | 50% heptane/50% THF | 0.36 | 0 |
| silica | 250 | 4.6 | 5 | 1 | 60% heptane/40% THF | 0.62 | 1.13 |
| silica | 250 | 4.6 | 5 | 1 | 70% heptane/30% THF | 1.22 | 1.15 |
| silica | 250 | 4.6 | 5 | 1 | 80% heptane/20% ethanol | 1.15 | 1.12 |
| silica | 250 | 4.6 | 5 | 1 | 80% heptane/20% ethanol | 0.76 | 1.09 |
| silica | 250 | 4.6 | 5 | 1 | 80% heptane/20% ethanol | 0.59 | 0 |
| silica | 250 | 4.6 | 5 | 1 | 80% heptane/20% ethanol | 0.74 | 1.0 |
| silica | 250 | 4.6 | 5 | 1 | 80% toluene/20% ethanol | 0.27 | 0 |

TABLE II-continued

Analysis of the separation of 1-nitro-3-benzyl-3-(N-ethoxy-carbonyl)amino-2-propanol diastereomers by conventional HPLC.

| Column Type | Length (mm) | Diameter (mm) | Particle size (μm) | Flow Rate (mL/min.) | Mobile Phase | $k_2'$ | α |
|---|---|---|---|---|---|---|---|
| silica | 250 | 4.6 | 5 | 1 | 80% toluene/ 20% THF | 0.55 | 1.14 |
| Chiralpak AD | 250 | 4.6 | 10 | 2–4 | 100% ethanol | 0.23 | 1.6 |
| Chiralpak AD | 250 | 4.6 | 10 | 2–4 | 90% ethanol/ 10% heptane | 0.19 | 1.7 |
| Chiralpak AD | 250 | 4.6 | 10 | 2–4 | 90% ethanol/ 10% iso-propanol | 0.23 | 1.4 |

Results from the separation of 1-nitro-3-(N-tert-butoxycarbonyl)amino-2-propanol diastereomers are presented in Table III.

TABLE III

Analysis of the separation of 1-nitro-3-benzyl-3-(N-tert-butoxy-carbonyl)amino-2-propanol diastereomers by conventional HPLC.

| Column Type | Length (mm) | Diameter (mm) | Particle size (μm) | Flow Rate (mL/min.) | Mobile Phase | $k_2'$ | α |
|---|---|---|---|---|---|---|---|
| C18 | 100 | 10 | 5 | 2–4 | 20% water/ 80% methanol | *NA | **NS |
| C18 | 100 | 10 | 5 | 2–4 | 30% water/ 70% methanol | 1.57 | 1.16 |
| C18 | 100 | 10 | 5 | 2–4 | 50% water/ 50% methanol | 4.6 | 1.09 |
| C18 | 250 | 10 | 5 | 2–4 | 20% water/ 80% methanol | 0.6 | 1.20 |
| C18 | 250 | 10 | 5 | 2–4 | 30% water/ 70% methanol | 1.64 | 1.21 |
| C18 | 250 | 10 | 5 | 2–4 | 40% water/ 60% acetonitrile | 2.01 | 1.12 |
| C18 | 250 | 10 | 5 | 2–4 | 50% water/ 50% acetonitrile | 4.12 | 1.77 |
| C18 | 250 | 4.6 | 5 | 1 | 40% water/ 60% methanol | 3.47 | 1.23 |
| C18 | 250 | 4.6 | 5 | 1 | 30% water/ 70% methanol | 1.16 | 1.23 |
| C18 | 250 | 4.6 | 5 | 1 | 20% water/ 80% methanol | *NA | **NS |
| Kromosil C-18 | 250 | 4.6 | 5 | 1 | 30% water/ 70% methanol | 2.16 | 1.20 |
| Divinyl benzene | 250 | 4.6 | 5 | 1 | 50% water/ 50% acetonitrile | *NA | **NS |
| Nucleosil ($NH_2$) | 250 | 4.6 | 5 | 1 | 50% water/ 50% acetonitrile | *NA | **NS |

TABLE III-continued

Analysis of the separation of 1-nitro-3-benzyl-3-(N-tert-butoxy-carbonyl)amino-2-propanol diastereomers by conventional HPLC.

| Column Type | Length (mm) | Diameter (mm) | Particle size (μm) | Flow Rate (mL/min.) | Mobile Phase | $k_2'$ | α |
|---|---|---|---|---|---|---|---|
| Phenyl | 250 | 4.6 | 5 | 1 | 40% water/ 60% acetonitrile | 0.66 | 1.1 |
| CN | 250 | 4.6 | 5 | 1 | 30% water/ 70% methanol | *NA | **NS |
| C3 | 250 | 4.6 | 5 | 1 | 50% water/ 50% methanol | 1.21 | 1.2 |
| silica | 250 | 4.6 | 5 | 1 | 95% heptane/ 5% iso-propanol | *NA | **NS |
| YMC PVA-Sil (silica) | 250 | 4.6 | 5 | 1 | 95% heptane/ 5% iso-propanol | 2.35 | 1.1 |
| Chiralpak AS | 250 | 4.6 | 10 | 2–4 | 100% ethanol | *NA | **NS |
| Chiralpak AD | 250 | 4.6 | 10 | 2–4 | 100% acetonitrile | *NA | **NS |
| Chirex 3001 | 50 | 4.6 | 5 | 1 | 95% heptane/ 5% iso-propanol | 7.6 | 1.3 |
| Chirex 3014 | 50 | 4.6 | 5 | 1 | 95% heptane/ 5% iso-propanol | 3.1 | 1.2 |
| Chirex 3022 | 50 | 4.6 | 5 | 1 | 70% heptane/ 30% iso-propanol | *NA | **NS |

*NA stands for not applicable.
**NS stands for no separation.

Results from the separation of 1-nitro-3-benzyl-3-(N-pheylmethoxycarbonyl)amino-2-propanol diastereomers are presented in Table IV.

TABLE IV

Analysis of the separation of 1-nitro-3-benzyl-3-(N-phenylmethoxycarbonyl)amino-2-propanol diastereomers by conventional HPLC.

| Column Type | Length (mm) | Diameter (mm) | Particle size (μm) | Flow Rate (mL/min.) | Mobile Phase | $k_2'$ | α |
|---|---|---|---|---|---|---|---|
| C18 | 250 | 4.6 | 5 | 1 | 40% water/ 60% acetonitrile | 2.02 | 1.08 |
| C18 | 250 | 4.6 | 5 | 1 | 30% water/ 70% iso-propanol | *NA | **NS |

*NA stands for not applicable
**NS stands for no separation

Example 4

Synthesis of 3-Benzyl-3-Amino-2-Hydroxypropanoic Acid Salt

3-Benzyl-3-(N-tert-butoxycarbonyl)amino-1-nitro-2-propanol was dissolved in 2.8 L of toluene/methanol (10:1). 500 mL of a 6M HCl solution was added to the mixture. The mixture was allowed to stirred at room temperature overnight. The layers were separated, and the aqueous layer was concentrated to dryness. 150 mL of a 12 M HCl solution was added to the concentrate, and the mixture was heated to 100° C. in a sealed container. The pressure was adjusted to 40 psi with HCl gas and the temperature and pressure were maintained for 20 hours. The mixture was cooled to 35° C. and diluted with $H_2O$ and filtered. The free base was formed by passing the fitrate through an ion-exchange column and concentrating the eluent to yield of 3-benzyl-3-amino-2- hydroxypropanoic acid. The desired salt was formed by addition of the appropriate acid.

Example 5

Determination of Simulated Moving Bed Separation Conditions for Separation of the HCl salt of 3-Benzyl-3-amino-2-Hydroxypropanoic Acid Diastereomers from Conventional HPLC Data The separation of the HCl salt of 3-benzyl-3-amino-2-hydroxypropanoic acid diastereomers was done using several mobile phase systems and several reverse phase columns. The results are summarized in Table V.

until all the diastereomers dissolved. The feed was then cooled to room temperature before separation.

Flowrates were measured in mass per time using a calibrated balance. A Mettler Toledo PB3001 balance calibrated using a NIST traceable standard was used to monitor the mobile phase and extract flowrates.

Figure 5A:
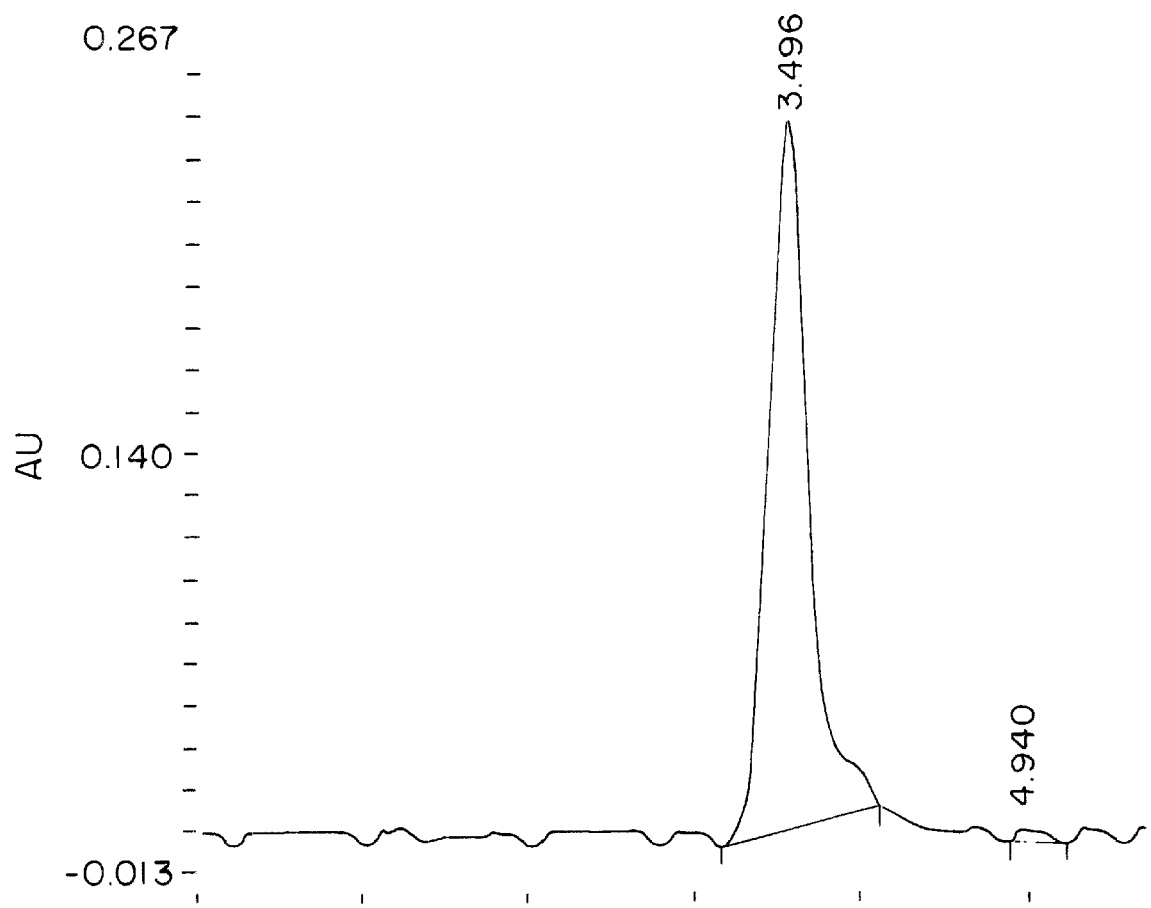
FIG. 5A is a chromatogram showing the purity of the more absorptive diastereomer of 1-nitro-3-benzyl-3-(N-ethoxycarbonyl)amino-2-propanol after separation by simulated moving bed chromatography.
Figure 5B:
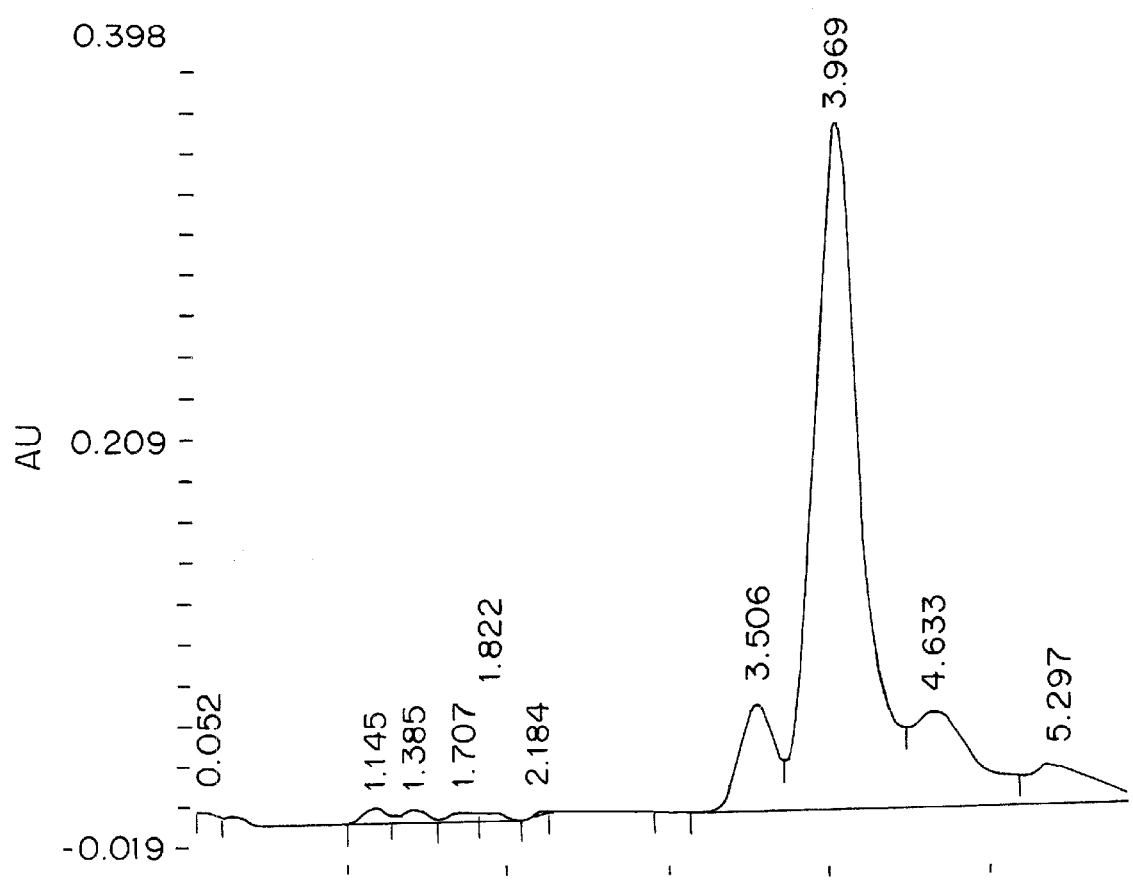
FIG. 5B is a chromatogram showing the purity of the less absorptive diastereomer of 1-nitro-3-benzyl-3-(N-ethoxycarbonyl)amino-2-propanol after separation by simulated moving bed chromatography.

The product was analyzed using a divinyl benzene column (length 10 cm, diameter 1.0 cm, particle size 10 $\mu$m) by conventional HPLC. The diastereomers were detected using a PDA detector set at 220 nM. The more absorptive diastereomer was recovered from the raffinate in greater than 99% purity (see FIG. 5A). The less absorptive diastereomer was recovered from the extract in 98% purity (see FIG. 5B).

TABLE V

Analysis of the separation of the HCl salt of 3-benzyl-amino-2-hydroxypropanoic acid diastereomers by conventional HPLC.

| Column Type | Length (mm) | Diameter (mm) | Particle size ($\mu$m) | Flow Rate (mL/min.) | Mobile Phase | $k_2'$ | $\alpha$ |
|---|---|---|---|---|---|---|---|
| C8 (symmetry) | 150 | 3.8 | 5 | 1 | 90% water/ 10% acetonitrile | 1.25 | 2.18 |
| C8 (symmetry) | 150 | 3.8 | 5 | 1 | 90% water/ 10% acetonitrile | 1.39 | 2.0 |
| C18 (Kromosil) | 250 | 4.6 | 5 | 1 | 90% water/ 10% acetonitrile | 1.86 | 2.0 |
| C18 (Kromosil) | 250 | 4.6 | 5 | 1 | 85% water/ 15% acetonitrile | 0.68 | 1.4 |

Example 6

Separation of 1-Nitro-3-Benzyl-3-(N-Ethoxycarbonyl)amino-2-Propanol Diastereomers Using Reverse Phase Simulated Moving Bed Chromatography From the method development data in Example 3, columns and mobile phase combinations which had an $\alpha$ value of 1.15 or greater where determined to be suitable for simulated moving bed separation of 1-nitro-3-benzyl-3-(N-ethoxycarbonyl)amino-2-propanol diastereomers or 1-nitro-3-benzyl-3-(N-tert-butoxycarbonyl)amino-2-propanol diastereomers. In general, greater solubility of the diastereomers in the mobile phase is desirable since it allows the diastereomers to be feed into the simulated moving bed columns through the feed line in a concentrated solution. In addition, shorter retention times (i.e., smaller k') for the diastereomers are preferred provided that $\alpha$ is 1.15 or greater because this shortens the cycle time for separation.

The 1-nitro-3-benzyl-3-(N-ethoxycarbonyl)amino-2-propanol diastereomers were separated on a Universal Pharma Technologies, LLC, SMB-L V.4. The SMB-L was configured with eight columns (inner diameter 2.12 cm, length 6.5 cm). Each column was slurry packed with divinyl benzene (particle size 20 $\mu$m) stationary phase supplied by Jordi Associates (Bellingham, Mass.). Mobile phase was prepared using ACS grade isopropanol and reagent grade heptane. Mobile phase was premixed in a stainless steel container and then charged to the SMB-L mobile phase tank.

Feed was prepared by dissolving the 1-nitro-3-benzyl-3-(N-ethoxycarbonyl)amino-2-propanol diastereomers in premixed mobile phase. The solution was heated to 40–50° C.

Details of the simulated moving bed method used to separate the 1-nitro-3-benzyl-3-(N-ethoxycarbonyl)amino-2-propanol diastereomers are summarized in Table VI.

TABLE VI

Parameters used for simulated moving bed separation of 1-nitro-3-benzyl-3-(N-ethoxycarbonyl)amino-2-propanol diastereomers.

| | |
|---|---|
| Column Diameter | 2.12 cm |
| Column Length | 6.5 cm |
| Number of Columns | 8 |
| Feed Concentration | 120 g/L |
| Eluent Flow Rate | 32 mL/min. |
| Extract Flow Rate | 8.11 mL/min. |
| Feed Flow Rate | 1.97 mL/min. |
| Raffinate Flow Rate | 25.86 mL/min. |

Example 7

Separation of 1-Nitro-3-Benzyl-3-(N-Ethoxycarbonyl)amino-2-Propanol Diastereomers Using Normal Phase Simulated Moving Bed Chromatography The SMB-L System is used to separate 1-nitro-3-benzyl-3-(N-ethoxycarbonyl)amino-2-propanol diastereomers using a sixteen column configuration. The columns used are normal phase Kromsil Silica columns (length 6.5 cm, diameter 2.1 cm, particle size 5 $\mu$m). The mobile phase used is 80% hexane/20% ethanol. A solution of the diastereomers (24.15 mg/mL) is fed onto the simulated moving bed columns at a rate of 7.5 mL/min. The extract rate is 11.18 mL/min., the total mobile phase rate is 57.22 mL/min., the fresh mobile phase rate is 13.87 mL/min., the raffinate flow rate is 10.20 mL/min., and the recycling flow rate is 43.35 mL/min. The cycle time was 10 minutes. The simulated moving bed separation conditions for separation of 1-nitro-3-benzyl-3-(N-ethoxycarbonyl)amino-2-propanol diastereomers are summarized in Table VII.

TABLE VII

Parameters for simulated moving bed separation of 1-nitro-3-benzyl-3-(N-ethoxycarbonyl)amino-2-propanol diastereomers.

| | |
|---|---|
| Column Length | 6.5 cm |
| Number of Columns | 16 |
| Feed Concentration | 24.15 mg/mL |
| Recycling Flow Rate | 43.35 mL/min. |
| Total Mobile Phase Flow Rate | 57.22 mL/mi. |
| Extract Flow Rate | 11.18 mL/min. |
| Feed Flow Rate | 7.51 mL/min. |
| Fresh Mobile Phase Flow Rate | 13.87 mL/min. |
| Raffinate Flow Rate | 10.20 mL/min. |

Equivalents

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of preparing a 1-nitro-3-substituted-3-amino-2-propanol diastereomer represented by the following structural formula:

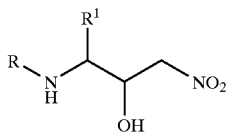

wherein:
R is an amine protecting group; and
$R^1$ is an amino acid side-chain, a protected amino acid side-chain, a substituted or unsubstituted aliphatic group, a substituted or unsubstituted aromatic group, a substituted or unsubstituted heteroaromatic group, a substituted or unsubstituted aralkyl or a substituted or unsubstituted heteroaralkyl group, comprising the steps of:
a) contacting a 3S or 3R 1-nitro-3-substituted-3-amino-2-propanone with a carbonyl reducing agent to form a mixture of two 1-nitro-3-substituted-3-amino-2-propanol diastereomers;
b) separating the 1-nitro-3-substituted-3-amino-2-propanol diastereomers by simulated moving bed chromatography to obtain:
 i) a first 1-nitro-3-substituted-3-amino-2-propanol diastereomer in at least 95% diastereomeric excess, and
 ii) a second 1-nitro-3-substituted-3-amino-2-propanol diastereomer or a mixture of the first 1-nitro-3-substituted-3-amino-2-propanol diastereomer and the second 1-nitro-3-substituted-3-amino-2-propanol diastereomer;
c) contacting the second 1-nitro-3-substituted-3-amino-2-propanol diastereomer or a mixture of the second 1-nitro-3-substituted-3-amino-2-propanol diastereomer and the first 1-nitro-3-substituted-3-amino-2-propanol diastereomer with an oxidizing agent to reform a 1-nitro-3-substituted-3-amino-2-propanone;
d) contacting the reformed 1-nitro-3-substituted-3-amino-2-propanone with a carbonyl reducing agent to form a second mixture of 1-nitro-3-substituted-3-amino-2-propanol diastereomers having a higher diastereomeric excess of the first 1-nitro-3-substituted-3-amino-2-propanol diastereomer than before oxidation; and
e) separating the second mixture of 1-nitro-3-substituted-3-amino-2-propanol diastereomers by simulated moving bed chromatography to afford the first 1-nitro-3-substituted-3-amino-2-propanol diastereomer in 95% diastereomeric excess, and the second 1-nitro-3-substituted-3-amino-2-propanol diastereomer or a mixture of the first 1-nitro-3-substituted-3-amino-2-propanol diastereomer and the second 1-nitro-3-substituted-3-amino-2-propanol diastereomer is recovered.

2. The method of claim 1 wherein the second 1-nitro-3-substituted-3-amino-2-propanol diastereomer or a mixture of the first 1-nitro-3-substituted-3-amino-2-propanol diastereomer and the second 1-nitro-3-substituted-3-amino-2-propanol diastereomer recovered is cyclically oxidized, reduced and separated by simulated moving bed chromatography until the first 1-nitro-3-substituted-3-amino-2-propanol diastereomer is recovered in at least about 90% yield.

3. A method of preparing a 1-nitro-3-substituted-3-amino-2-propanol diastereomer represented by the following structural formula:

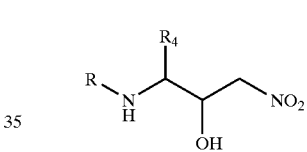

wherein:
R is an amine protecting group; and
$R^4$ is an amino acid side-chain or a protected amino acid side-chain, comprising the steps of:
a) contacting an amino acid having a protected amine group with a carboxylic acid activator, thereby forming an activated amino acid;
b) contacting the activated amino acid with a nitromethane anion solution to form a reaction mixture;
c) adding an acid to the reaction mixture, thereby forming a 1-nitro-3-substituted-3-amino-2-propanone;
d) contacting a 1-nitro-3-substituted-3-amino-2-propanone with a carbonyl reducing agent to form a mixture of 1-nitro-3-substituted-3-amino-2-propanol diastereomers; and
e) separating the 1-nitro-3-substituted-3-amino-2-propanol diastereomers by simulated moving bed chromatography to obtain one or more 1-nitro-3-substituted-3-amino-2-propanol diastereomer.

4. The method of claim 3, wherein the protected amino acid is an L-isomer or a D-isomer, and a mixture of two 1-nitro-3-substituted-3-amino-2-propanol diastereomers is formed when the 1-nitro-3-substituted-3-amino-2-propanone is contacted with the carbonyl reducing agent.

5. A method of preparing a 1-nitro-3-benzyl-3-amino-2-propanol diastereomer represented by the following structural formula:

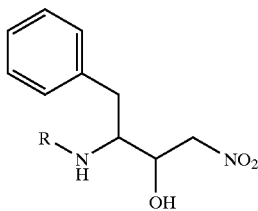

wherein:

R is an amine protecting group, comprising the steps of:
  a) contacting phenylalanine having a protected amine group with a carboxylic acid activator, thereby forming an activated phenylalanine;
  b) contacting the activated phenylalanine with a nitromethane anion solution to form a reaction mixture;
  c) adding an acid to the reaction mixture, thereby forming a 1-nitro-3-benzyl-3-amino-2-propanone;
  d) contacting the 1-nitro-3-benzyl-3-amino-2-propanone with a carbonyl reducing agent to form a mixture of 1-nitro-3-benzyl-3-amino-2-propanol diastereomers; and
  e) separating the 1-nitro-3-benzyl-3-amino-2-propanol diastereomers by simulated moving bed chromatography to obtain one or more 1-nitro-3-benzyl-3-amino-2-propanol diastereomer.

6. A method of preparing a diastereomer of a 3-substituted-3-amino-2-hydroxypropanoic acid salt represented by the following structural formula:

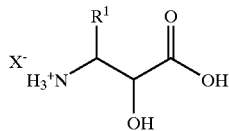

wherein:

$X^-$ is $Cl^-$, $Br^-$, $F^-$, $I^-$, $^-HSO_4$, or $^-H_2PO_4$;

$R^1$ is an amino acid side-chain, a protected amino acid side-chain, a substituted or unsubstituted aliphatic group, a substituted or unsubstituted aromatic group, a substituted or unsubstituted heteroaromatic group, a substituted or unsubstituted aralkyl or a substituted or unsubstituted heteroaralkyl group, comprising the steps of:
  a) contacting a mixture of 1-nitro-3-substituted-3-amino-2-propanol diastereomers with an acid to form a mixture of 3-substituted-3-amino-2-hydroxypropanic acid diastereomeric salts; and
  b) separating the 3-substituted-3-amino-2-hydroxypropanic acid diastereomeric salts by simulated moving bed chromatography to obtain one or more 3-substituted-3-amino-2-hydroxypropanoic diastereomeric salt.

7. The method of claim 6, wherein the simulated moving bed has a reverse phase solid support.

8. The method of claim 7, wherein the reverse phase solid support is a C18 solid support.

9. The method of claim 6, wherein the simulated moving bed has a normal phase solid support.

10. The method of claim 6, wherein the simulating moving bed has a chiral solid support.

11. The method of claim 6, wherein the simulating moving bed has an ion-exchange solid support.

12. A method of preparing a diastereomer of a 3-substituted-3-amino-2-hydroxypropanoic acid salt represented by the following structural formula:

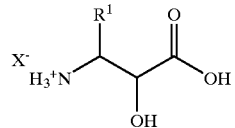

wherein:

$X^-$ is $Cl^-$, $Br^-$, $F^-$, $I^-$, $^-HSO_4$, or $^-H_2PO_4$;

$R^1$ is an amino acid side-chain, a protected amino acid side-chain, a substituted or unsubstituted aliphatic group, a substituted or unsubstituted aromatic group, a substituted or unsubstituted heteroaromatic group, a substituted or unsubstituted aralkyl or a substituted or unsubstituted heteroaralkyl group, comprising the steps of:
  a) separating a mixture of 1-nitro-3-substituted-3-amino-2-propanol diastereomers by simulated moving bed chromatography; and
  b) contacting a diastereomer of 1-nitro-3-substituted-3-amino-2-propanol diastereomer obtained in step a) with an acid to form a 3-substituted-3-amino-2-hydroxypropanic acid diastereomeric salt.

* * * * *

UNITED STATES PATENT AND TRADEMARK OFFICE
CERTIFICATE OF CORRECTION

PATENT NO.    : 6,462,221 B1
DATED         : October 8, 2002
INVENTOR(S)   : Richard L. Gabriel et al.

It is certified that error appears in the above-identified patent and that said Letters Patent is hereby corrected as shown below:

<u>Title page,</u>
Item [73], Assignee, please delete "Pharm-Eco Laboratories, Inc., Devens, MA (US)" and insert -- Johnson Matthey Pharmaceutical Materials, Inc., Devens, MA (US) --.

Signed and Sealed this

Twenty-sixth Day of August, 2003

JAMES E. ROGAN
*Director of the United States Patent and Trademark Office*